United States Patent
van der Linde

(10) Patent No.: US 9,489,278 B2
(45) Date of Patent: Nov. 8, 2016

(54) FIELD DEVICE

(71) Applicant: KROHNE Messtechnik GmbH, Duisburg (DE)

(72) Inventor: Martin van der Linde, Oberhausen (DE)

(73) Assignee: KROHNE Messtechnik GmbH, Duisburg (DE)

( * ) Notice: Subject to any disclaimer, the term of this patent is extended or adjusted under 35 U.S.C. 154(b) by 426 days.

(21) Appl. No.: 14/133,729

(22) Filed: Dec. 19, 2013

(65) Prior Publication Data

US 2014/0257756 A1 Sep. 11, 2014

(30) Foreign Application Priority Data

Mar. 8, 2013 (DE) .................. 10 2013 102 327

(51) Int. Cl.
| | |
|---|---|
| H03F 1/26 | (2006.01) |
| G06F 11/30 | (2006.01) |
| G05B 19/042 | (2006.01) |
| G01F 1/00 | (2006.01) |
| G01N 33/00 | (2006.01) |

(52) U.S. Cl.
CPC .............. *G06F 11/30* (2013.01); *G01F 1/00* (2013.01); *G01N 33/00* (2013.01); *G05B 19/0428* (2013.01); *G05B 2219/24015* (2013.01); *G05B 2219/24021* (2013.01); *G05B 2219/25428* (2013.01)

(58) Field of Classification Search
CPC . G11B 7/246; G11B 7/24079; G11B 7/2467; G11B 7/2472; G11B 7/2492; G11B 7/2495; G11B 7/2534; G11B 2007/24612; G11B 7/00736; G11B 7/2533; G11B 7/259; G11B 7/00456; G11B 7/00455; G11B 7/24094
See application file for complete search history.

(56) References Cited

U.S. PATENT DOCUMENTS

| | | | |
|---|---|---|---|
| 6,954,717 B2 | 10/2005 | Boldt et al. | |
| 7,987,297 B2 | 7/2011 | Schwabe et al. | |
| 2008/0126145 A1* | 5/2008 | Rackley, III | ......... G06Q 20/102 455/406 |
| 2011/0319166 A1* | 12/2011 | Bathiche | ................. A63F 13/12 463/40 |

FOREIGN PATENT DOCUMENTS

| | | |
|---|---|---|
| DE | 10 2005 062 418 A1 | 5/2007 |
| DE | 102006062603 A1 | 7/2008 |
| DE | 10 2010 028 152 A1 | 10/2011 |
| EP | 0 964 325 B1 | 8/2002 |
| WO | 2011/131752 A1 | 10/2011 |

* cited by examiner

*Primary Examiner* — Roy Y Yi
(74) *Attorney, Agent, or Firm* — David S. Safran

(57) ABSTRACT

A field device that provides a field device that allows the simplest possible logging of relevant operational data. The field device has at least one data storage device (3) designed as an integral component of the field device and a control unit designed as an integral component of the field device (1). In this case, the control unit stores a data set in the data storage device (3) depending on a monitoring event.

11 Claims, 3 Drawing Sheets

FIELD DEVICE

BACKGROUND OF THE INVENTION

1. Field of the Invention

The invention relates to a field device, for example, for a measurement device for determining a measured or process variable or an actuator for adjusting or controlling a process variable or a corresponding surrounding condition.

2. Description of Related Art

In modern process automation, processes are monitored or controlled with different field devices. Such field devices—designed as measurement devices or as actuators—are implemented either as stand-alone devices or they are connected, for example, via a field bus, with a process control system (PCS). Communication buses, for example, field buses according to the Profibus- or HART standard, are used for communication with such a PCS or a control room included by a PCS. Furthermore, field devices can still be differentiated by whether they have a common interface with two wires or different interfaces with a total of four (or more) wires for data communication and power supply. Accordingly, such devices are also referred to as two- or four-wire devices.

Despite all the efforts and improvements, it is or cannot always be out ruled that errors occur, that unforeseen events occur or that field devices are used outside their specifications. Furthermore, it may be advantageous or necessary that conditions are recorded, and thus, documented. Moreover, it is advantageous for improving the quality of the field devices, when detailed information about continuous operation is provided.

To gain access to the existing data in the field devices, for example, the European Patent EP 0 964 325 B1 discloses a method, in which status or diagnostic data from field devices is collected and transmitted to an evaluation unit. A problem here is that the amount of data provided by the field devices can possibly be very high, so that the data bus between the field devices and a control room can be very busy. This is particularly problematic when the field devices only have a limited amount of energy available. Moreover, such a method is generally not possible in field devices that are connected to a data bus. Moreover, it is not necessarily desired that all of the data, for example, concerning the process to be monitored and controlled, be transmitted via a field bus.

As an alternative, for example, the German Patent Application DE 10 2005 062 418 A1 describes a separate data logger that can be connected to a field device and allows local data logging. A disadvantage is that this is an additional component that has to be connected to the field device.

SUMMARY OF THE INVENTION

A primary object of the present invention is, thus, to provide a field device that allows a very simple logging of relevant operational data, while avoiding the disadvantages of the prior art.

The field device according to the invention, in which the previously derived and shown object is achieved, is initially and substantially wherein the field device comprises at least one data storage device designed as an integral component of the field device and at least one control unit designed as an integral component of the field device. Thereby, the control unit stores at least one data set in the data storage device depending on at least one predetermined monitoring event.

The field device according to the invention has a built-in data logger, which is supplied with data by a control unit intrinsic in the field device. So that not all data generated or obtained or occurring in the field device are recorded, at least one monitoring event is predetermined, at the occurrence of which, the control unit stores, i.e., saves at least one data set in the data storage device matching this monitoring event. The control unit may be an additional component in the field device, but it can also be represented by central intelligence of the field device, i.e., can be implemented, for example, as part of an overall processing unit. The data that is to be stored with each data set can, in one design, be specifically chosen using a filter or alternatively, for example, be exactly predefined during manufacture of the field device.

The following designs deal especially with different monitoring events. Here, each single monitoring event can lead to storage of at least one data set. Alternatively, several monitoring events are specified, whose occurrence leads respectively to at least one data set being stored.

In one design, the monitoring event is an error condition being present in the field device. For this purpose, it is accordingly necessary that it is detected in the field device that an error exists. This can be implemented by running diagnostic programs or in that abnormal values, e.g., voltage drops or jumps in the current etc., are identified. The self-monitoring of field devices, for example, is described in the NAMUR recommendation NE 107, entitled "Self-monitoring and Diagnostics of Field Devices."

In a further design, at least one measuring unit is provided for determining at least one measured variable. For this, the monitoring event comprises a value of the measured variable determined by the measuring unit being outside a predetermined interval. In this design, the field device is a measuring device for determining or monitoring a measured variable (for example, fill level, flow rate, pH, temperature, viscosity, electrical conductivity or oxygen content of a medium). The associated monitoring event is the presence of a measured value outside an interval, such as the exceeding of a threshold value. Such an interval may be provided, for example, by the specification of the device or the components used or possibly due to determining algorithms providing the measured variable.

In an additional design, at least one sensor unit is provided for determining at least one secondary measured variable. For this, the monitoring event is the value of the secondary measured variable determined by the sensor unit being outside a predetermined range.

The actual or primary measured variable depends in part on other additional process variables. This is, for example, the temperature of the medium when determining the flow rate of a medium or its pH value. Furthermore, the measurement units for the primary measured variable can even be affected by another process variable, so that an associated measurement is required or indicated. Thus, for example, sensor components of the measuring unit allow only safe use within certain conditions. However, such a secondary measured variable may, in a field device in the form of an actuator, consist of this measured variable determining if the engaging action of the actuator is successful. At least one corresponding predetermined interval is also set for this secondary measured variable, which represents a monitoring event when it is exceeded, which is logged by the control unit according to the invention in the data storage means as a data set.

If, in one design of the measuring unit determining the fill level, the flow rate or the pH is formed as a measured variable, then another alternative or additional design provides that the sensor unit for detecting the temperature or pressure is used as the secondary measured variable. Further measured variables and a corresponding design of the measuring unit or the sensor unit are self-evident and can be implemented by components of the prior art.

In another design, the field device has at least one access interface for allowing access to said field device. This is, for example, a so-called service interface, which allows, for example, the import of software or firmware and via which, in particular, the transmission of larger amounts of data is possible, e.g., for scanning of data sets of the data storage device.

Alternatively, this is a user interface in the form of a so-called man-machine interface, access to the field device being possible via its display and the implementation of an input possibility. Thus, for example, individual parameters can be selected or modified according to the application from a series of predefined parameters.

In this context, it is provided as a possible monitoring event in such an access interface that via the access interface (generally) access and/or (specifically and thus so chosen) a particular type of access takes place on the field device. In this variation, influence on the field device is logged.

In a particular design, in which a specific type of influence is provided on the field device as a monitoring event, in the event that at least one operating parameter of the field device is changed via the access interface, the control unit stores at least data about the point in time of the change or data about the operating parameters or a value of the operating parameter given before the change or data about instances changing the operating parameters in the data storage device as a data set.

The data set that is stored in the data storage device for the occurrence of the monitoring event "change at least one parameter", thus comprises at least a type of time stamp, an indication about the modified parameters, the old and/or new value or an identification means for the person or general instance that made the change. A timestamp can originate from a clock located in the field device or time information transmitted to the field device, for example, via the bus connection. The modified parameters can be stored in a data set using encoding. Correspondingly, the old or new values can be stored using absolute or relative information. An indication of the modification instance is particularly relevant when a parameter change is not possible for an arbitrary group of people, but is reserved for individuals or specified groups of people. Thus, if a particular access code is required then, for example, this or the associated authorization is stored in the data set associated with the monitoring event.

Storing the data as part of a data set or data sets is explained in greater detail in the following designs.

The control unit stores several pieces of predetermined data of the field device as a data set, wherein the data is at least one of a value associated with the monitoring event, or an indication of a point in time, or a value associated with a sequence of the occurrence of the monitoring event, or an indication of an operating time of the field device, or at least one value for a measured variable determined by the field device, or at least one value generated and/or calculated within the field device. The data can be selected by a user in one design and, in an alternative design, is optimally selected depending on the amount of space available for storage in the data storage device and/or the amount of energy available for storage.

The data of the data set characterizes, on the one hand, the monitoring event in relation to an encoding of each monitoring event or its occurrence. In this manner, for example, a counter for the frequency of the event is maintained or it is logged by whether the monitoring event occurred after an initialization or during operation.

On the other hand, the data is a "snapshot" of the conditions of the field device or the process, insofar as other measured variables, currently calculated or determined values, intermediate values, etc., are stored. In addition, there is optionally an indication about the operating time of the field device or which measured variables or process parameters existed before the occurrence of the monitoring event.

Moreover, it may also be necessary or helpful, if the data set or the data sets associated with the monitoring event relate to data or measured values occurring after the trigger or previous to it. If, for example, the monitoring event represents an exceptional reading, it can be advantageous, for example, to pursue which measurement accuracy can be achieved using the data sets stored in the data storage device. Alternatively, if an interval is exceeded for the secondary measured variable, the impact on and, in particular the consequences for the actual measurement can be identified by logging the values of the primary measured variable.

In a further design, an impact of the parameter change on the measurements can be recognized and, especially can be verified according to a change in a measured parameter by logging the determined value of the primary measured variable.

In one design in particular, it is provided that, after an occurrence of the monitoring event, the control unit stores a predetermined number of additional data sets in conjunction with the occurrence of the monitoring event in the data storage device. During evaluation, this data allows for observation of the impact of the monitoring event on the field device, or on its data, or even generally on the process that measures the field device or is engaged by it.

If the monitoring event extends over a certain period of time, the control unit is formed in such a manner in one design that it, in this case, stores at least one data set in the data storage device when the monitoring event is completed. In this design, a snapshot is logged after the end of the monitoring event.

Alternatively or additionally, in a further design, in the case of a prolonged monitoring event, the control unit stores at least the duration of the existence or presence of the monitoring event as a data set and/or as part of a data set in the data storage device. Here, at least the duration of the monitoring event is stored.

If a monitoring event is repeated, the control unit saves the number of occurrences of the monitoring event in the data storage device as a data set or part of a data set in one design in the case of a repeated occurrence. Thus, in this design, the control unit takes note of how often the event takes place. Depending on the type of monitoring event, different designs can also correspondingly be combined with one another.

This running of a counter is especially advantageous when each occurrence of the monitoring event is not saved in the data storage device, but is partially deleted or overwritten due to the space available for storage or for the reduction of stored data sets, in particular for evaluation.

Thus, in the event of a repeated occurrence of a monitoring event, if the monitoring event occurs, one embodiment consists of the control unit overwriting or deleting in the data storage device at least one data set saved for a previous occurrence of the monitoring event. In this design, not all data sets belonging to the same type of monitoring event and being saved before the current occurrence are saved, but at least one previous and therefore older data set is deleted or overwritten by each new data set.

The first occurrence of the monitoring event or its associated monitoring data can, for example, be excluded, so that this data set is maintained. Further criteria can be set that guarantee safeguarding of a data set.

In one design, the control unit is made familiar with the conditions that characterize the existence of a monitoring event in a so-called learning phase. This is done, for example, using the input of specific, observed threshold values or in that the conditions that are accessible to the field device, for example, a measured variable, are approached, while the field device takes measurements in this learning phase or acts upon a process as an actuator.

In one design, it is provided that the control unit stipulates a number and/or size of the data of the data set depending on a storage size of the data storage device and/or the amount of storage available for storing the data set on the data storage device. Since the data storage device is a part of the field device and is therefore subject to appropriate limitations, the control unit in this design scales the number of data sets to be deposited or their sizes to the data storage available in each case.

If, in particular, several monitoring events are to be logged, the available space in the data storage device must be taken into account under certain circumstances. Furthermore, it may occur that two monitoring events occur simultaneously or in close temporal proximity. It is, thus, provided in one design, that the different monitoring events are given different levels of importance, i.e., have different priority values. The monitoring events are quasi provided with different significances. Based on these levels of importance or the different priorities, the control unit then stores the data sets associated with the monitoring events in the data storage device. For example, a monitoring event with a higher priority is assigned a larger space for more data to be stored than a monitoring event with a lower priority.

With the specification of several different monitoring events, it is also provided in one design that two differently constructed types of data sets are stored for at least two different monitoring events. The data sets differ here especially with regard to the structure of the data, such as the sequence of the individual data or its size in terms of minimum and/or maximum size. In this design, the data sets are fitted or optimized for the associated monitoring event. In a further design, a special type of data set is provided for each monitoring event.

Conversely, data storage and reading or evaluating of the data from the data storage device in the case that several monitoring events are defined can be simplified in that the control unit stores the data sets of all monitoring events as the same type of data set in the data storage device. For all, or at least for all the selected, quasi activated monitoring events in this design, at least one data set of the same form or, respectively, the same structure is stored.

Since the monitoring events with regard to the data available or, respectively, relevant for assessment can be differentiated from one another, it is provided in one design that the control unit replenishes at least a part of the data of a data set that is free from a value in a monitoring event with at least a placeholder when storing the data set. This results in at least constantly uniform data sets that are accessible for evaluation or processing.

Since the memory capacity in a data storage device is limited for technical reasons, the control unit in one design uses the data storage device in the manner of a ring buffer, so that the oldest data sets are overwritten. Here, in one design, individual data sets or at least one data set is protected specifically against being written over or deleted.

For storage or saving of data sets, the control unit in one design conforms to a predefined data set structure that partitions the available memory of the data storage device or defines individual sections.

Alternatively, the control unit stores the data sets sequentially or the data of the data sets is stored in incoherent sections of the data storage device.

In order to read the data sets and, possibly, individual pieces of data from the data storage device—as an alternative or as a supplement to a data storage device removable from the field device—the field device in one design has at least one data interface for read access to the data storage device.

The data interface in one design is one via which the field device can be connected to a control room or a field bus. In one design, a central unit of the field device communicates with the data interface and accesses—if necessary, via the control unit—the data to the data storage device.

For such access via such a data interface or for reading the data of a data storage device taken out of the field device, it is provided in one design that not all of the data or data sets can be freely accessed, but rather that at least one stored data set or part of a stored data set can be read only after release from the data storage device. This release can occur, for example, by entering a corresponding release code.

One design is connected with a data-reading procedure, in which the control unit stores the occurrence of read access as a data set and/or as part of a data set in the data storage device when read access occurs. Thus, for example, a mark for reading is set, when the data set has been read.

In one design, the data storage device, or at least a part of it, can be removed from the field device and accordingly re-inserted. If, for example, this is a memory card, it is removed from the field device, the data is extracted by a computer, and then it is re-placed into the data storage device.

To achieve security of stored data sets, the data storage device in one design is encapsulated within the field device, i.e. against influences that affect the field device, once again protected separately. Preferably, the encapsulation is such that access to the stored data sets is possible even if part of the field device is destroyed.

The above designs and embodiments are strongly correlated to a field device that is designed as a measuring device in order to determine or monitor a measuring variable. Here, the above designs, however, also relate to a field device that is formed as an actuator in order to influence at least one process variable. Therefore, in one design, at least one engagement unit for adjusting at least one process variable is provided. The engaging unit is, for example, a valve, around a heating or cooling device or a barrier, etc.

In one design, the field device is designed as a two-wire device, so that energy supply and data transmission take place via the same connection. Alternatively, the field device is designed as a four-wire device. In another variation, it is a stand-alone unit, which is additionally provided with a power storage unit and in a further design, additionally with a unit for "energy harvesting".

In detail, there are a variety of possibilities for designing and further developing the field device according to the present invention as will be apparent from the following description of embodiments in conjunction with the accompanying drawings.

DETAILED DESCRIPTION OF THE INVENTION

Figure 1:
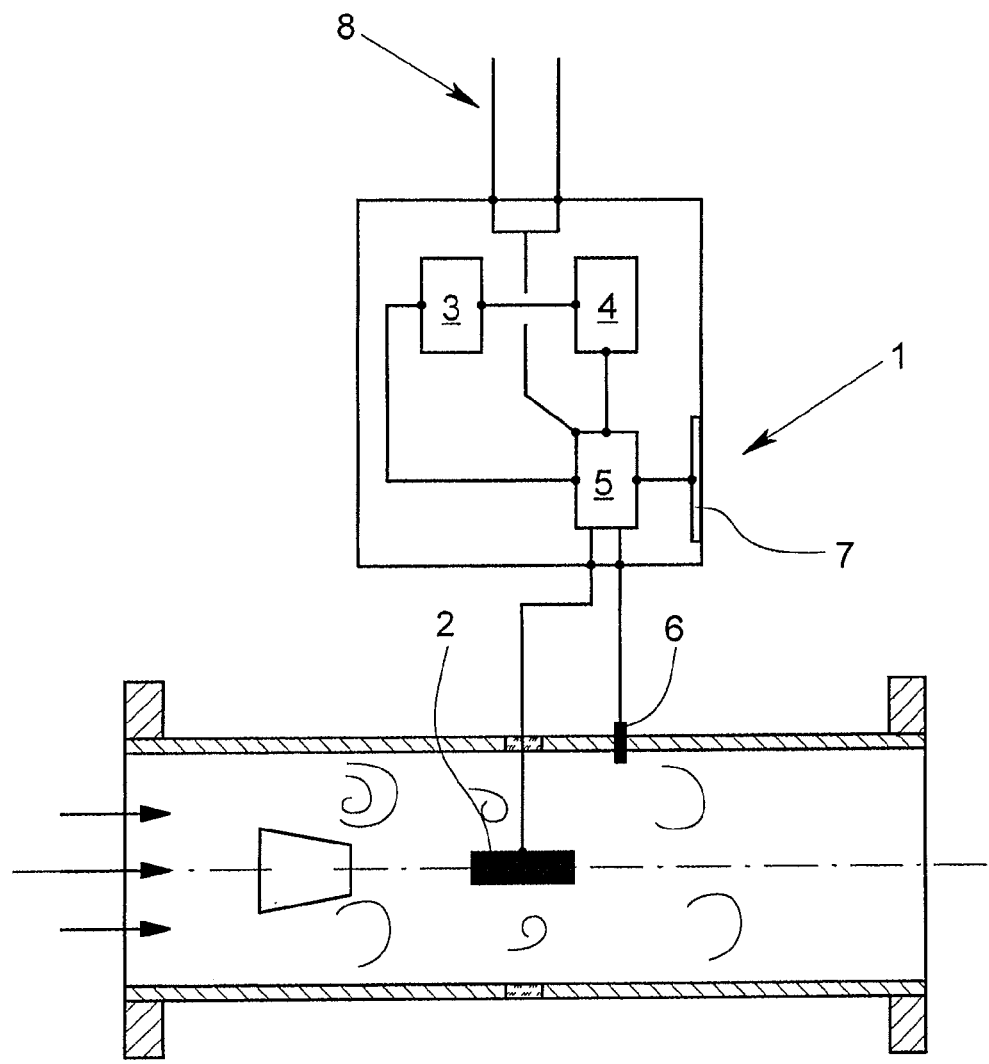
FIG. 1 is a schematic representation of a field device according to the invention in a first embodiment, essentially showing the functional relationships and partially designed in block diagram.

A first embodiment of a field device 1 according to the invention is shown in FIG. 1. In this embodiment, the field device 1 is a measuring device for determining a measured variable or monitoring this variable. A measuring unit 2 is provided here for this measurement. In the embodiment shown here, the measuring unit 2 determines, in particular, pressure fluctuations that occur due to a vortex in a flowing medium (indicated by the arrows).

The flow is measured overall using the vortex principle. This measuring principle is based on a so-called Karman vortex street that can form behind a bluff body in a flowing medium with medium flowing by it in a measuring tube, in that vortices are formed, separated from the bluff body and carried along by the current. The frequency at which the vortices are separated is dependent on the rate of flow, wherein the ratio, under certain conditions, is almost linear. By measuring the vortex frequency with a measuring unit 2, the rate of flow of the medium can be determined.

A data storage device 3 and a control unit 4 are provided in the field device 1 as integral parts. Integral means that these components are present in the field device 1 and are required for completeness. Thus, they are not, for example, additionally added.

The control unit 4 has access at least to log data or store it on the data storage device 3, so that appropriate connections are provided.

For the operation of the field device 1, and in particular, for carrying out the measurements of the measuring unit 2, a central processing unit 5 is provided as a primary control unit of the field device 1. In an alternative embodiment (not shown), the control unit 4 is a part of the central processing unit 5 or the central processing unit 5 assumes the functions of the control unit 4. The control unit 4 receives the data from the central processing unit 5 or the control unit 4 accesses the data that it stores in the data storage device 3 in the presence of the monitoring event, or one of the predetermined monitoring events.

The control unit 4 stores data sets in the data storage device 3 in dependence on predetermined monitoring events. This storing or saving is purely a procedure internal to the field-device that is performed by the field device 1 itself with integral components of the field device 1. Which data is involved—particularly an encoding of the monitoring event, a time stamp, a snapshot of the data present in the field device 1, etc.—will be made clearer below. Depending on the application or the type of monitoring event, the data is chosen or, respectively, is filtered out of the amount of all possible data present in the field device.

In one variation, there are a plurality of potential monitoring events, which are selected from a predetermined list or individually defined for the type of the field device 1 and the type of application. A monitoring event can be characterized by a condition, such as, e.g., the occurrence of a measured value or the triggering of an event. Alternatively, however, this can also be a complex state that is characterized by the occurrence of several conditions.

Possible monitoring events are, for example, the presence of an error condition in the field device 1, data access to the field device 1, the occurrence of a measured value outside a predetermined interval for the measuring variable to be measured by the measurement unit 2, or the presence of a measured value outside of a specified range of values that is determined with a sensor unit 6 for a secondary measuring variable.

The sensor unit 6 is used here, for example, for temperature measurement, so that the control unit 4 stores a data set in the data storage device 3 and a predetermined temperature range specified for the use of the field device 1. Such a range can optionally be adequately described using only a threshold value.

Alternatively or additionally, data sets are created and stored depending on the operating time of the field device 1. In other embodiments, data concerning the operating time is stored within data sets linked with corresponding monitoring events. In one embodiment, operating time is logged in more detail, the data sets concerning the operating are stored depending on the values of the measured variable—here the flow—measured with the measuring unit 2. Thus, a kind of extended operation time logging is carried out, for example, in also logging how often and over what period of time the measured variable was located within specified intervals. The individual specified intervals, for example, partially sit in one another, or are adjacent to one another, or possibly partly overlap. This enables the effect of the process variable on the device itself to be taken into account, e.g., a greater effect on the device from higher process temperatures than from lower ones.

With such a fine structure of the sequence of the measured variables or process conditions, an observation of the strain on the field device 1 is possible or, respectively, it can be assessed if the field device 1 has been operated within predefined specifications. For this latter consideration, the determination of the secondary measured variable via the sensor unit 6 is used as a measure for the process or measuring conditions.

Another possible monitoring event is that access to the field device 1 takes place using an access interface 7.

In one embodiment, the access interface 7 is a so-called service interface, via which data can be input and output. In an alternative embodiment, it is a user interface (so-called human-machine interface, HMI) with a display and visualized keys (e.g., a replica of a traditional keyboard or selection keys such as "right"/"left", "up"/"down" and "confirm"). In another embodiment—not shown—the access interface 7 is a fieldbus interface, e.g., for communication with a process control room.

If such access takes place via an access interface 7, or if there is intervention in the process of the field device 1, this can be evaluated—depending on the selection—as the occurrence of a monitoring event needing to be monitored, for which a corresponding data set is to be stored in the data storage device 3.

In this case, either each access is logged by storing a data set or there is a restriction to specific requests, such as changing operating or measuring parameters of the field device 1. The relevant data in such a parameter change are, e.g., the changed parameters or a code for these, the previous value of the parameter, or possibly also the value at which the parameter was set. If such a parameter change is also reserved for only individual persons or groups and they are required to identify themselves before a change, this reservation is also preferably stored in the corresponding data set. Furthermore, the field device 1 has, in this embodiment, a data interface 8, which is a two-wire interface here, and therefore, is also the power supply of the field device 1.

Data or data sets can be read from the data storage device 3 via this data interface 8—in the case shown, conveyed by the central unit 5. Here, the possible access to certain data sets, which, e.g., are assigned to certain monitoring events, is restricted or not all data or data sets are available for each access. Thus, in one specification, it is necessary that a release activity to be specified is carried out. In this embodiment, this means that a release code is sent to the field device 1—preferably via the access interface 7 or via the data interface 8, itself.

Figure 2:
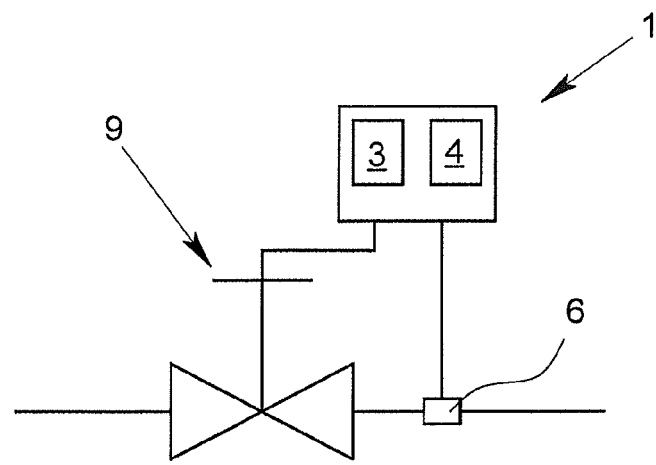
FIG. 2 is a schematic representation of a field unit according to the invention in a second embodiment.

FIG. 2 shows a field device 1 according to the invention, which is configured as an actuator. In this case, a valve is provided as an intervention unit 9 for the flow of a medium through an indicated line. A pressure gauge is used in this embodiment as sensor unit 6 for determining or monitoring a secondary—or rather, since this variation of the field device 1 does not require primary measured variable, only—measured variable. A data storage device 1 and a control unit 4 for storing data in the data storage device 3 are also provided in this field device 1.

Figure 3:
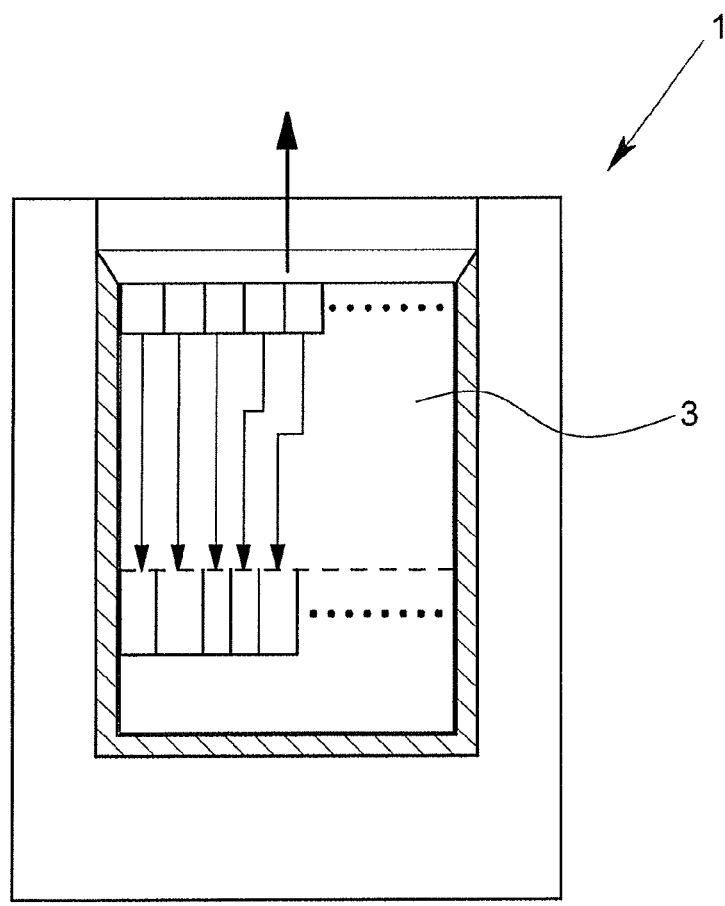
FIG. 3 is a schematic representation of a part of a field device according to the invention.

FIG. 3 shows, purely schematically, a part of a field device 1 according to the invention. The data storage device 3 is enclosed, in particular in case of damage, within the field device 1 and can be reversibly removed (indicated by the upward arrow) and then replaced.

Five data sets are also shown, purely symbolically, that have been stored in each case due to the occurrence of different monitoring events. The data sets are formed of two parts, stored in different locations of the data storage device 3. This is indicated here by the upper and the lower half of the memory.

The data structure is such that each of the data sets has the same head with the same sequence of basic data and a body with a scope designed for the respective monitoring event. Here, a link (indicated by the arrows) allows for the connection between head and body.

It can be seen that the bodies have different sizes. This is due, in the illustrated embodiment, to different data in respect to the current state of the field device being stored for the individual monitoring events or, respectively, the occurrence of the monitoring event.

Such a "snapshot" of the field device 1 or the prevailing process conditions can vary, depending on the type of monitoring event. For the monitoring event "parameter change" other data are obviously relevant for the monitoring event than for "exceeding a predetermined value for the process temperature as secondary measured variable". Thus, in the embodiment shown here, the storage of data occurs using different dimensions for the body of a data set.

In—not shown here—the case that all data sets, regardless of the specific monitoring event, have the same data size, possible fields are filled with placeholders. For example, if the change of parameters is logged with the same data sets as the exceeding of a threshold value, the data locations for the data of the changed parameters are filled with placeholders when the exceeding of a threshold value occurs.

The five data sets are stored sequentially in the data storage device 3 shown here. In an alternative version, a separate area of memory of the data storage device 3 is allocated for each monitoring event or at least each type of monitoring event. In another version, the data are respectively stored so that all sections of the memory are used about the same rate in order to avoid a kind of fatigue of the sections due to a frequently occurring writing and overwriting.

Figure 4:
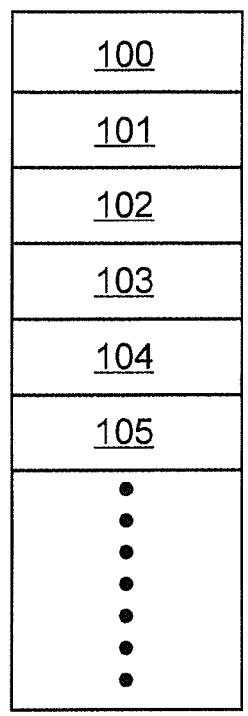
FIG. 4 is a schematic representation of the components of a data set.

In FIG. 4, a data set is indicated with the data contained in it.

In the top block 100, a value or a code is entered for each monitoring event.

The block 101 is followed by a status code that sets the occurrence of the monitoring event in relation to its "background". Details will follow in the description of FIG. 5.

This is followed, in block 102, by a counter, which detects the occurrence of the monitoring event. In repetitive monitoring events, possible individual, older data sets may also be deleted or overwritten.

In data blocks 100 to 102, for example, the head of the data set—as shown in FIG. 3—is stored separately from the respective body.

In blocks 103, 104, 105, etc., this is followed by individual data of a "snapshot" of the field device or process conditions. This is, for example, among other things, the value of the primary measured variable, the value of the secondary measured variable, the interim values calculated for each individual measured variable, the relevant and, particularly, set parameters, the measurement uncertainty of the individual values of the measured variables, etc. Such data is particularly advantageous in the case that the monitoring event is set as the exceeding of an interval by a value of a measured variable.

When logging a change of parameters, these data are, e.g., a value that identifies the parameters involved as a code, an old value of the parameter and the new value of the parameter and possibly an identification of the instance making the change with respect to the access authorization or in relation to a particular person.

In general, the data is stored as a "snapshot", which is particularly important as basic conditions for each monitoring event. Therefore, it is obvious that the data of the associated data sets can be significantly different for different monitoring events to be monitored and to be logged.

Figure 5:
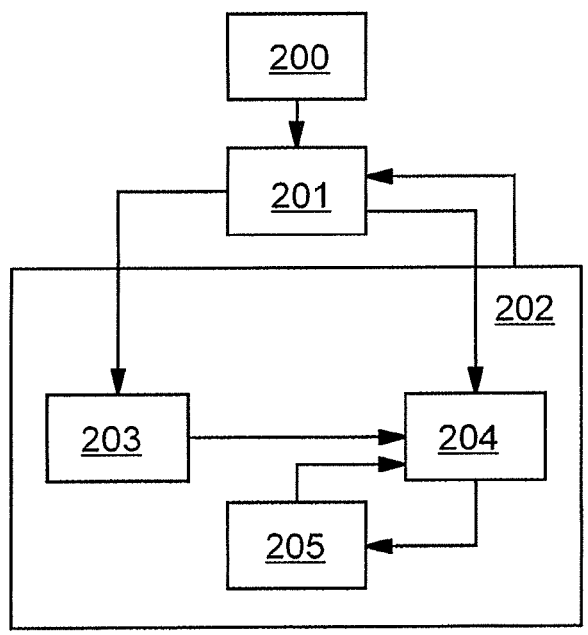
FIG. 5 is a schematic flow chart for the temporal sequence of occurrences of a monitoring event.

FIG. 5 shows a possible sequence for quantifying the occurrence of monitoring events, for which a corresponding status code (in FIG. 4, in block 101) is then stored in the data set. The presence of the monitoring event here is seen as an exceptional state for further inspection, which should not occur or does not occur during normal operation.

Initial operation startup of the field device starts in point 200.

For each of the following steps: 201 to 205, a counter for the status code is set at an appropriate value in the data set.

Thus, initialization is carried out at point 201, for which the status code is set to zero. This is followed by normal operation of the field device, the steps being arranged in block 202. Here, for this block 202, it is possible to reset the field device with a re-initialization back to the initial step 201 (indicated by the arrow back from block 202 to block 201).

In the case that the monitoring event does not occur, i.e., the normal state follows the initialization in step 201, step 203 is logged in that the status code is set to the value one.

If the monitoring event occurs after initialization, step 204 follows, in which the status code is set to the value two.

Since the monitoring event represents an exception to the normal behavior, preferably the monitoring event disappears again. Thus, in step 205, the status code is set to four in the sense that the system or the field device is no longer in the state that characterizes the monitoring event.

After steps 203 or 205, however, the conditions for the monitoring event and step 204 may occur again.

If such a relapse into the monitoring event (path from step 204 via 205 to 204) or a first-time occurrence of the monitoring event (path from step 203 to 204) takes place, the status code is increased accordingly in one variation, in order to characterize this transition path. In an alternative variation, the status code is set to the value two in both cases. However, it is logged by a counter for the occurrence of the monitoring event that, as it were, a relapse has occurred.

All in all, the status code, possibly in conjunction with the counter for the number of occurrences of the monitoring event, allows a quick overview of the behavior of the field device or the processes in the surroundings in which the device is used.

When storing these counters, the control unit 4, in one embodiment, also partly uses the data sets stored in the data storage device 3 to get necessary information about the previous monitoring events.

What is claimed is:

1. Field device for process automation, comprising:
   at least one data storage device formed as an integral component of the field device and
   at least one control unit formed as an integral component of the field device,
   wherein the control unit is adapted for storing at least one data set in the data storage device depending on at least one predeterminable monitoring event,
   wherein at least one measuring unit for determining at least one measured process variable is provided, and
   wherein the monitoring event comprises a value of the measured process variable determined by the measuring unit being outside a predetermined interval.

2. Field device according to claim 1, wherein at least one sensor unit for detecting at least one secondary measured variable is provided and wherein the monitoring event comprises a value of the at least one secondary measured variable determined by the sensor unit being outside a predetermined interval.

3. Field device according claim 1, wherein at least one access interface for enabling access to the field device is provided and wherein the monitoring event comprises at least one of access to the field device and a particular type of access to the field device taking place via the access interface.

4. Field device according claim 1, wherein the control unit is adapted to store predetermined data of the field device as a data set, wherein the predetermined data is at least one of a value associated with the monitoring event, a value associated with a point in time, a value associated with a sequence of occurrences of the monitoring event, information about the operating time of the field device, at least one value determined by the field device for a measured variable, and at least one value generated or calculated within the field device.

5. Field device according to claim 4, wherein the control unit stipulates at least one of a quantity and size of the data of the data set depending on at least one a storage size of the data storage device available for storing the data set and energy available for storing the data set.

6. Field device according claim 1, wherein, after an occurrence of the monitoring event, the control unit is adapted for storing a predetermined number of additional data sets in conjunction with the occurrence of the monitoring event in the data storage device.

7. Field device according claim 1, wherein the control unit is adapted for storing the number of occurrences of the monitoring event as a data set or as part of a data set in the data storage device.

8. Field device according claim 1, wherein the control unit is adapted for overwriting or deleting at least one data set for a previous occurrence of the monitoring event from data storage device when the monitoring event is repeated.

9. Field device according claim 1, wherein at least one data interface for read access to the data storage device is provided and wherein the control unit is adapted for storing the occurrence of the read access in the data storage device as a data set or as part of a data set when read access to the data storage device occurs.

10. Field device according to claim 2, wherein at least one engagement unit is provided for setting at least one process variable.

11. Field device according claim 1, wherein at least one measuring unit has means for determining at least one of fill level, flow rate, pH, temperature, viscosity, electrical conductivity and oxygen content of a medium as said at least one measured variable.

* * * * *